United States Patent
Calik et al.

(10) Patent No.: US 12,091,658 B2
(45) Date of Patent: Sep. 17, 2024

(54) ALCOHOL DEHYDROGENASE 2 (ADH2) PROMOTER VARIANTS BY PROMOTER ENGINEERING

(71) Applicant: ORTA DOGU TEKNIK UNIVERSITESI, Ankara (TR)

(72) Inventors: Pinar Calik, Ankara (TR); Burcu Gunduz Ergun, Ankara (TR)

(73) Assignee: ORTA DOGU TEKNIK UNIVERSITESI, Ankara (TR)

( * ) Notice: Subject to any disclaimer, the term of this patent is extended or adjusted under 35 U.S.C. 154(b) by 804 days.

(21) Appl. No.: 17/276,186

(22) PCT Filed: Sep. 23, 2019

(86) PCT No.: PCT/TR2019/050784
§ 371 (c)(1),
(2) Date: Mar. 15, 2021

(87) PCT Pub. No.: WO2020/068019
PCT Pub. Date: Apr. 2, 2020

(65) Prior Publication Data
US 2021/0309990 A1    Oct. 7, 2021

(30) Foreign Application Priority Data
Sep. 24, 2018 (TR) .................... 2018/13725

(51) Int. Cl.
*C12N 15/10* (2006.01)
*C07K 14/39* (2006.01)
(Continued)

(52) U.S. Cl.
CPC ............ *C12N 15/102* (2013.01); *C07K 14/39* (2013.01); *C12N 1/14* (2013.01); *C12N 15/815* (2013.01);
(Continued)

(58) Field of Classification Search
CPC ...... C12N 15/102; C12N 1/14; C12N 15/815; C07K 14/39; C12R 2001/78; C12R 2001/72; C12R 2001/88; C12R 2001/84
See application file for complete search history.

(56) References Cited

U.S. PATENT DOCUMENTS 6,730,499 B1    5/2004  Cregg
7,816,509 B2   10/2010  Lee et al.
(Continued)

FOREIGN PATENT DOCUMENTS

WO    2015158808 A2   10/2015
WO    2017021541 A1    2/2017
(Continued)

OTHER PUBLICATIONS

Walther and Schuller. "Adr1 and Cat8 synergistically activate the glucose-regulated alcohol dehydrogenase gene ADH2 of the yeast Saccharomyces cerevisiae" Microbiology. (2001). 147. p. 2037-2044 (Year: 2001).*
(Continued)

*Primary Examiner* — Evelyn Y Pyla
*Assistant Examiner* — Katherine R Small
(74) *Attorney, Agent, or Firm* — Bayramoglu Law Offices LLC

(57) ABSTRACT

*Pichia pastoris* alcohol dehydrogenase 2 (ADH2) promoter variants include at least one of the specified modifications on wild-type *Pichia pastoris* ADH2 promoter (SEQ ID NO: 1). The modification includes one of the following mutations: integration of a Cat8 transcription factor binding site (TFBS), particularly integration of SEQ ID NO: 3 or other gene sequences that show at least 80% similarity with this sequence, at any positions within nucleotides a) 647 to 660;
(Continued)

b) 739 to 752; c) 1 to 948; and d) mutations specified with SEQ ID NO: 2 within nucleotides 15 to 848 separately and combinations thereof.

14 Claims, 5 Drawing Sheets

Specification includes a Sequence Listing.

(51) Int. Cl.
  *C12N 1/14* (2006.01)
  *C12N 15/81* (2006.01)
  *C12R 1/72* (2006.01)
  *C12R 1/78* (2006.01)
  *C12R 1/84* (2006.01)
  *C12R 1/88* (2006.01)

(52) U.S. Cl.
  CPC ...... *C12R 2001/72* (2021.05); *C12R 2001/78* (2021.05); *C12R 2001/84* (2021.05); *C12R 2001/88* (2021.05)

(56) References Cited

U.S. PATENT DOCUMENTS

| | | |
|---|---|---|
| 8,222,386 B2 | 7/2012 | Cregg et al. |
| 8,785,613 B2 | 7/2014 | Cregg et al. |
| 9,279,129 B2 | 3/2016 | Hartner et al. |
| 2011/0129874 A1 | 6/2011 | Tsutsumi et al. |

FOREIGN PATENT DOCUMENTS

| | | | | |
|---|---|---|---|---|
| WO | WO-2017021541 A1 | * | 2/2017 | ............... C12N 1/16 |
| WO | WO-2019203769 A1 | * | 4/2018 | ........... C12N 15/815 |

OTHER PUBLICATIONS

Sequence Alignment Seq ID No. 1 Instant Application (ADH2) To Seq ID No. 1 In an WO 2019203769 A1(ADH3) (Year: 2024).*

Franz S. Hartner, et al., Promoter library designed for fine-tuned gene expression in Pichia pastoris. Nucleic Acids Research, 2008, pp. e76-e76, vol. 36 No. 12.

Bing Li, et al., The Role of Chromatin during Transcription, Cell, 2007, pp. 707-719, vol. 128.

Kevin Struhl, et al., Determinants of nucleosome positioning, Nature structural and molecular biology, 2013, pp. 267-273, vol. 20 No. 3.

Liqun Xi, et al., Predicting nucleosome positioning using a duration Hidden Markov Model, BMC Bioinformatics, 2010, pp. 1-9, 11:346.

Kathleen A. Curran, et al., Design of synthetic yeast promoters via tuning of nucleosome architecture. Nature Communications, 2014, pp. 1-8, 5:4002.

Joseph Sambrook, et al., Molecular cloning: a library manual, 2001, pp. 1.116-1.118, 3rd ed., vol. 1, Cold Spring Harbor Library Press, New York.

Invitrogen, EasySelect™ Pichia Expression Kit For Expression of Recombinant Proteins Using pPICZ and PPICZα in Pichiapastoris, User Manual, 2010, pp. 1-86, Cat. No. K1740-01.

Mudassar Ahmad, et al., Protein expression in Pichia pastoris: recent achievements and perspectives for heterologous protein production, Applied Microbiology and Biotechnology, 2014, pp. 5301-5317, vol. 98 No. 12.

Fidan Erden-Karaoglan, et al., Deletion analysis of Pichia pastoris alcohol dehydrogenase 2 (ADH2) promoter and development of synthetic promoters, Biotechnology Journal, 2021, pp. 1-14.

Burcu Gunduz Ergun, et al., Engineered Deregulation of Expression in Yeast with Designed Hybrid-Promoter Architectures in Coordination with Discovered Master Regulator Transcription Factor, Advanced Biosystems, 2020, pp. 1-12.

Burcu Gunduz Ergun, et al., Engineering of alcohol dehydrogenase 2 hybrid-promoter architectures in Pichia pastoris to enhance recombinant protein expression on ethanol, Biotechnology and Bioengineering, 2019, pp. 1-13.

Valerie Haurie, et al., The Transcriptional Activator Cat8p Provides a Major Contribution to the Reprogramming of Carbon Metabolism during the Diauxic Shift in Saccharomyces cerevisiae, The Journal of Biological Chemistry, 2001, pp. 76-85, vol. 276 No. 1.

Margit Hiesinger, et al., Contribution of Cat8 and Sip4 to the transcriptional activation of yeast gluconeogenic genes by carbon source-responsive elements, Current Genetics, 2001, pp. 68-76, vol. 39.

Balla Venkata Kranthi, et al., Identification of key DNA elements involved in promoter recognition by Mxr1p, a master regulator of methanol utilization pathway in Pichia pastoris, Biochimica et Biophysica Acta, 2009, pp. 460-468.

Roland Prielhofer, et al., Superior protein titers in half the fermentation time: Promoter and process engineering for the glucose-regulated GTH1 promoter of Pichia pastoris, Biotechnology and Bioengineering, 2018, pp. 2479-2488.

Antje Rahner, et al., Deregulation of gluconeogenic structural genes by variants of the transcriptional activator Cat8p of the yeast Saccharomyces cerevisiae, Molecular Microbiology, 1999, pp. 146-156, vol. 34 No. 1.

Stephanie Roth, et al., Transcriptional activators Cat8 and Sip4 discriminate between sequence variants of the carbon source-responsive promoter element in the yeast Saccharomyces cerevisiae, Current Genetics, 2004, pp. 121-128, vol. 45.

Christine Tachibana, et al., Combined Global Localization Analysis and Transcriptome Data Identify Genes That Are Directly Coregulated by Adr1 and Cat8, Molecular and Cellular Biology, 2005, pp. 2138-2146, vol. 25 No. 6.

Miguel C. Teixeira, et al., YEASTRACT: an upgraded database for the analysis of transcription regulatory networks in Saccharomyces cerevisiae, Nucleic Acids Research, 2018, pp. 348-353, vol. 46.

Kristin Walther, et al., Adr1 and Cat8 synergistically activate the glucose-regulated alcohol dehydrogenase gene ADH2 of the yeast Saccharomyces cerevisiae, Microbiology, 2001, pp. 2037-2044, vol. 147.

Ji-Ping Wang, et al., Preferentially Quantized Linker DNA Lengths in Saccharomyces cerevisiae, PLoS Computational Biology, 2008, pp. 1-10, vol. 4.

Liqun Xi, et al., MPertehoddoilcogtyi anrtigcle nucleosome positioning using a duration Hidden Markov Model, BMC Bioinformatics, 2010, pp. 1-9, vol. 11.

* cited by examiner

SEQUENCE No 1

>P_ADH2-wt

"TCCTTTTACCACCAAGTGCGAGTGAAACACCCATGGTCTGCTCCGATTGCCCCTCTACAGGCATAA
GGGTGTGACTTTGTGGGCTTGAATTTTACACCCCCTCCAACTTTTCTGCATCAATTGATCCTGTTACCAA
TATTGCATGCCGGAGGAGACTTGCCCCTAATTGCGGCGTCCGGATCGCGTGTCGAGGGTGAGACTGT
AGAGACCCCACATAGTGACAATGATTATGTAAGAAGAGAGGGGTGATTCGGCCGGCTATCGAACTCTAA
CAACTAGGGGGGTGAACAATGCCCAGCAGTCCTCCCACTCTTTGACAAATCAGTATCACCGATTAACAC
CCCAAATCTTATTCTCAACGGTCCCTCATCCTTGCACCCCTCTTTGGACAAATGGCAGTTAGCATTGGTGC
ACTGACTGCCCAACCTTAAACCCAAATTTCTAGAAGGGCCCATCTAGTTAGCGAGGGGTGAAA
AATTCCTCCATCGGAGATGTATTGACCGTAAGTGCTGTTAAAAAATCAGTTCAGATAGCGAGACTTT
TTTGATTTCGCAACGGGAGTGCCTGTTCCATTCGATTGCAATTCTCACCCCTTCTGCCAGTCCTGCCAAT
TGCCCATGAATCTGTAATTCGTTGATTCCCCACTACATAAAGGCGACGGTTGTCGAAAAGATCTGTAGTTTTCAA
CATTTGGGAGAATCTGCATGTCCCCGCTGTTTGAAAACGGGGGTGAGCGCTCCGGGGTGCGAATTCGTGCCAAT
TCCTTTCACCCTGCTATTGTAGACGTCAACCGCATCTGGTGCAAATTCACCTTCTAATATTCAGTCACAGCGCACCCCAATGATCACA
CCAACAATTGGTCCCCCCAATCTCTAATATTCACAATTCACCTCTATTACTTACTTCCTGCT
CCCAAATTCTTTTTCCTTCTCCATCAGTCAGCTACTAGCTTTATCTTATTTACTTTACGAAA"

FIG. 4

SEQUENCE No 2

>P_ADH2-NucOpt

TCCTTTTACCACCTAAGTGGGAGTGAAACACCCTATGGGTGCTGTCTCCGATTGCCCCTCTACAGGCATAAGGG
TGTGATTTTTTTTTAATTTTACACCCCCTCCAACTTTTCGTAAATTGATCCGTTACCAATATTGCAT
GCCCGGAGGAGACTTGCCCCTAATTGCGGGCGTGTCTCCGGATGCGCAGGGTAAAAATATATAGACCCCA
CAAAAAAAATGATTATGTAAGAAGAGAGGGGTGATTCGGCCGGCTATCGAACTCTAACAACTAGGGGGG
TGAAAATGCCCAGCTTTTCCCTATCTTTGACAAATCAGTATCACTATTAACACCCAAATTTTTTCTCA
ACGGTCCCTCATCGTTGCCACCCCTCTTTGGACACTAGTATTAGTCACTGACTGCCTAACC
TAAACCCTAATTTCTTAGAAGGGGCCCATATAGTTAGCGAGGGCCCATAGATAGCGAAATTTTTTGATTCGGACGCGGTTTTT
TTTTTTTTTTTTTTTTTTTCTCACCCCTCTGCCCAGTTCTGCCATGAATCTACTAATTTCGTTGATTC
CCACCCCCCCTTCCAACTCCAAAATTTTTTTTTAATTTTTTTTTGGGAGAATCGAATGTATATTACATAA
AGCGACCGGTGTCCGAAAATTTTTTTTTTCCCCGCTTTTAAAAACGGGGGT
AAGCGGCTCTCCGGGGTGCGAATTCGGCCCTATTCCTTTCACCCTGCCTATTGTAGACGTCAACCCGCATCTG
GTGCGGAATATAGGCACCCCAATGATCACACCAACAATTGGTCCACCCCTCTAATTCTAATATTCACAATT
CACCTCACTATAAATACCCCGTCCCAAATTCTTTTCCTTTCCATCAGCTACTAGCTTTTATCTTAT
TTACTTTTACGAAA"

* Modified positions in the design of nucleosome optimized ADH2 promoter variant, P_ADH2-NucOpt are represented with bold and underlined characters.

FIG. 5

SEQUENCE LISTING

<160> NUMBER OF SEQ ID NOS: 13

<210> SEQ ID NO 1
<211> LENGTH: 1047
<212> TYPE: DNA
<213> ORGANISM: Pichia pastoris

<400> SEQUENCE: 1

```
tccttttttac cacccaagtg cgagtgaaac accccatggc tgctctccga ttgcccctct      60
acaggcataa gggtgtgact ttgtgggctt gaatttttaca cccccctccaa cttttctcgc     120 atcaattgat cctgttacca atattgcatg cccggaggag acttgccccc taatttcgcg     180
gcgtcgtccc ggatcgcagg gtgagactgt agagacccca catagtgaca atgattatgt     240
aagaagaggg gggtgattcg gccggctatc gaactctaac aactaggggg gtgaacaatg     300
cccagcagtc ctccccactc tttgacaaat cagtatcacc gattaacacc ccaaatctta     360
```

| | | |
|---|---|---|
| ttctcaacgg tccctcatcc ttgcacccct ctttggacaa atggcagtta gcattggtgc | 420 | |
| actgactgac tgcccaacct taaacccaaa tttcttagaa ggggcccatc tagttagcga | 480 | |
| ggggtgaaaa attcctccat cggagatgta ttgaccgtaa gttgctgctt aaaaaaaatc | 540 | |
| agttcagata gcgagacttt tttgatttcg caacgggagt gcctgttcca ttcgattgca | 600 | |
| attctcaccc cttctgccca gtcctgccaa ttgcccatga atctgctaat ttcgttgatt | 660 | |
| cccacccccc tttccaactc cacaaattgt ccaatctcgt tttccatttg ggagaatctg | 720 | |
| catgtcgact acataaagcg accggtgtcc gaaagatct gtgtagtttt caacattttg | 780 | |
| tgctcccccc gctgtttgaa aacgggggtg agcgctctcc ggggtgcgaa ttcgtgccca | 840 | |
| attcctttca ccctgcctat tgtagacgtc aacccgcatc tggtgcgaat atagcgcacc | 900 | |
| cccaatgatc acaccaacaa ttggtccacc cctccccaat ctctaatatt cacaattcac | 960 | |
| ctcactataa ataccctgt cctgctccca aattcttttt tccttcttcc atcagctact | 1020 | |
| agctttatc ttatttactt tacgaaa | 1047 | |

<210> SEQ ID NO 2
<211> LENGTH: 1047
<212> TYPE: DNA
<213> ORGANISM: Artificial Sequence
<220> FEATURE:
<223> OTHER INFORMATION: P ADH2-NucOpt

<400> SEQUENCE: 2

| | | |
|---|---|---|
| tccttttac cacctaagtg cgagtgaaac accctatggc tgctctccga ttgcccctct | 60 | |
| acaggcataa gggtgtgatt ttttttttt taatttaca cccctccaa cttttttcgc | 120 | |
| gtaaattgat cctgttacca atattgcatg cccggaggag acttgccccc taatttcgcg | 180 | |
| gcgtcgtccc ggatcgcagg gtaaaaatat atagacccca caaaaaaaa atgattatgt | 240 | |
| aagaagaggg gggtgattcg gccggctatc gaactctaac aactaggggg gtgaaaaatg | 300 | |
| cccagctttt ttcccctattc tttgacaaat cagtatcact tattaacacc ccaaatttt | 360 | |
| ttctcaacgg tccctcatcc ttgcacccct ctttggacaa atggcagtta gtattagtgc | 420 | |
| actgactgac tgcctaacct taaaccctaa tttcttagaa ggggcccata tagttagcga | 480 | |
| ggggtgaaaa attcctccat cggagatgta ttaaccgtaa tttttttttt aaaaaaaaa | 540 | |
| aattcagata gcgaaatttt tttgatttcg cgacgcgcgt tttttttttt tttttttttt | 600 | |
| tttctcaccc cttctgccca gttctgccaa ttgcccatga atctactaat ttcgttgatt | 660 | |
| cccacccccc tttccaactc caaaaatttt ttaattttt ttttttttg ggagaatctg | 720 | |
| aatgtatatt acataaagcg accggtgtcc gaaaaatttt tttttttt taattttttt | 780 | |
| tttttccccc gcttttaaa aacgggggta agcgctctcc ggggtgcgaa ttcgcgccct | 840 | |
| attcctttca ccctgcctat tgtagacgtc aacccgcatc tggtgcgaat atagcgcacc | 900 | |
| cccaatgatc acaccaacaa ttggtccacc cctccccaat ctctaatatt cacaattcac | 960 | |
| ctcactataa ataccctgt cctgctccca aattcttttt tccttcttcc atcagctact | 1020 | |
| agctttatc ttatttactt tacgaaa | 1047 | |

<210> SEQ ID NO 3
<211> LENGTH: 14
<212> TYPE: DNA
<213> ORGANISM: Artificial Sequence
<220> FEATURE:
<223> OTHER INFORMATION: Cat8 transcription factor binding site

<400> SEQUENCE: 3
ttccgttcgt ccga                                                  14

<210> SEQ ID NO 4
<211> LENGTH: 1047
<212> TYPE: DNA
<213> ORGANISM: Artificial Sequence
<220> FEATURE:
<223> OTHER INFORMATION: P ADH2-Cat1 (P ADH2-Cat8-L1)

<400> SEQUENCE: 4

| | | |
|---|---|---|
| tccttttac cacccaagtg cgagtgaaac accccatggc tgctctccga ttgcccctct | 60 |
| acaggcataa gggtgtgact ttgtgggctt gaattttaca cccctccaa cttttctcgc | 120 |
| atcaattgat cctgttacca atattgcatg cccggaggag acttgccccc taatttcgcg | 180 |
| gcgtcgtccc ggatcgcagg gtgagactgt agagacccca catagtgaca atgattatgt | 240 |
| aagaagaggg gggtgattcg gccggctatc gaactctaac aactaggggg gtgaacaatg | 300 |
| cccagcagtc ctccccactc tttgacaaat cagtatcacc gattaacacc ccaaatctta | 360 |
| ttctcaacgg tccctcatcc ttgcaccct ctttggacaa atggcagtta gcattggtgc | 420 |
| actgactgac tgcccaacct aaacccaaa tttcttagaa ggggcccatc tagttagcga | 480 |
| ggggtgaaaa attcctccat cggagatgta ttgaccgtaa gttgctgctt aaaaaaaatc | 540 |
| agttcagata gcgagacttt tttgatttcg caacgggagt gcctgttcca ttcgattgca | 600 |
| attctcaccc cttctgccca gtcctgccaa ttgcccatga atctgcttcc gttcgtccga | 660 |
| cccacccccc tttccaactc cacaaattgt ccaatctcgt tttccatttg ggagaatctg | 720 |
| catgtcgact acataaagcg accggtgtcc gaaaagatct gtgtagtttt caacattttg | 780 |
| tgctcccccc gctgtttgaa aacgggggtg agcgctctcc ggggtgcgaa ttcgtgccca | 840 |
| attcctttca ccctgcctat tgtagacgtc aacccgcatc tggtgcgaat atagcgcacc | 900 |
| cccaatgatc acaccaacaa ttggtccacc cctccccaat ctctaatatt cacaattcac | 960 |
| ctcactataa ataccctgt cctgctccca aattctttt tccttcttcc atcagctact | 1020 |
| agcttttatc ttatttactt tacgaaa | 1047 |

<210> SEQ ID NO 5
<211> LENGTH: 1047
<212> TYPE: DNA
<213> ORGANISM: Artificial Sequence
<220> FEATURE:
<223> OTHER INFORMATION: P ADH2-Cat2 (P ADH2-Cat8-L2)

<400> SEQUENCE: 5

| | | |
|---|---|---|
| tccttttac cacccaagtg cgagtgaaac accccatggc tgctctccga ttgcccctct | 60 |
| acaggcataa gggtgtgact ttgtgggctt gaattttaca cccctccaa cttttctcgc | 120 |
| atcaattgat cctgttacca atattgcatg cccggaggag acttgccccc taatttcgcg | 180 |
| gcgtcgtccc ggatcgcagg gtgagactgt agagacccca catagtgaca atgattatgt | 240 |
| aagaagaggg gggtgattcg gccggctatc gaactctaac aactaggggg gtgaacaatg | 300 |
| cccagcagtc ctccccactc tttgacaaat cagtatcacc gattaacacc ccaaatctta | 360 |
| ttctcaacgg tccctcatcc ttgcaccct ctttggacaa atggcagtta gcattggtgc | 420 |
| actgactgac tgcccaacct aaacccaaa tttcttagaa ggggcccatc tagttagcga | 480 |
| ggggtgaaaa attcctccat cggagatgta ttgaccgtaa gttgctgctt aaaaaaaatc | 540 |
| agttcagata gcgagacttt tttgatttcg caacgggagt gcctgttcca ttcgattgca | 600 |

```
attctcaccc cttctgccca gtcctgccaa tgcccatga atctgctaat ttcgttgatt    660 cccaccccc tttccaactc cacaaattgt ccaatctcgt tttccatttg ggagaatctg    720
catgtcgact acataaagtt ccgttcgtcc gaaaagatct gtgtagtttt caacattttg    780
tgctcccccc gctgtttgaa aacggggtg agcgctctcc ggggtgcgaa ttcgtgccca    840
attcctttca ccctgcctat tgtagacgtc aacccgcatc tggtgcgaat atagcgcacc    900
cccaatgatc acaccaacaa ttggtccacc cctccccaat ctctaatatt cacaattcac    960
ctcactataa ataccctgt cctgctccca aattcttttt tccttcttcc atcagctact   1020
agcttttatc ttatttactt tacgaaa                                       1047
```

<210> SEQ ID NO 6
<211> LENGTH: 63
<212> TYPE: DNA
<213> ORGANISM: Artificial Sequence
<220> FEATURE:
<223> OTHER INFORMATION: Primer

<400> SEQUENCE: 6

```
cctgccaatt gcccatgaat ctgcttccgt tcgtccgacc cacccccctt tccaactcca    60
caa                                                                  63
```

<210> SEQ ID NO 7
<211> LENGTH: 63
<212> TYPE: DNA
<213> ORGANISM: Artificial Sequence
<220> FEATURE:
<223> OTHER INFORMATION: Primer

<400> SEQUENCE: 7

```
ttgtggagtt ggaaaggggg gtgggtcgga cgaacggaag cagattcatg ggcaattggc    60
agg                                                                  63
```

<210> SEQ ID NO 8
<211> LENGTH: 38
<212> TYPE: DNA
<213> ORGANISM: Artificial Sequence
<220> FEATURE:
<223> OTHER INFORMATION: Primer

<400> SEQUENCE: 8

```
gtcgactaca taaagttccg ttcgtccgaa aagatctg                            38
```

<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9

```
cagatctttt cggacgaacg gaactttatg tagtcgac                            38
```

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10

```
gtcggatccc tgcagtcctt tttac                                          25
```

<210> SEQ ID NO 11
<211> LENGTH: 44
<212> TYPE: DNA
<213> ORGANISM: Artificial Sequence
<220> FEATURE:
<223> OTHER INFORMATION: Primer

<400> SEQUENCE: 11
gcccttgctc accattttcg taaagtaaat aagataaaag ctag         44

<210> SEQ ID NO 12
<211> LENGTH: 42
<212> TYPE: DNA
<213> ORGANISM: Artificial Sequence
<220> FEATURE:
<223> OTHER INFORMATION: Primer

<400> SEQUENCE: 12 caaaaacaa ctaattattc gaaacgaatg gtgagcaagg gc           42

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
cgaggtacct tacttgtaca gctcgtcc                          28

ALCOHOL DEHYDROGENASE 2 (ADH2) PROMOTER VARIANTS BY PROMOTER ENGINEERING

CROSS REFERENCE TO THE RELATED APPLICATIONS

This application is the national phase entry of International Application No. PCT/TR2019/050784, filed on Sep. 23, 2019, which is based upon and claims priority to Turkish Patent Application No. 2018/13725, filed on Sep. 24, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBUY129-Sequence Listing.txt and is 8,158 bytes in size.

TECHNICAL FIELD

The present invention is related to enhanced original alcohol dehydrogenase 2 (ADH2) gene promoter-variants designed by promoter engineering.

BACKGROUND

Promoter genes are DNA nucleotide sequences that initiate and continue recombinant protein synthesis within the promoter architecture and that are necessary upstream DNA elements for protein expression. The number, quality, functional position of the transcription factor binding sites available on promoter genes, and the transcription factors which bind to these positions and the interaction between them are the fundamental components of the promoter architecture.

The strength of the promoter genes determines the recombinant protein production capacity of the host cells. Industrial recombinant protein production with the yeast *Pichia pastoris* (*P. pastoris*) has started in 1981 and in the last 10 years this is the yeast on which most research has been conducted. The phytase (Phytex, Sheridan, IN, USA) used in the feed industry, trypsin for proteomics studies (Roche Applied Science, GERMANY), nitrate reductase for water analysis and treatment (The Nitrate Elimination Co., Lake Linden, MI, USA), phospholipase C used in degumming of vegetable oils (Verenium, San Diego, CA, USA/DSM, Holland), collagen used in health research and as dermal filling (Fibrogen, San Francisco, CA, USA), and proteinase K (Thermo Scientific, Waltham, MA, USA) are recombinant proteins that are already being produced with the prior art by *P. pastoris* (Ahmad et al., 2014). The first biopharmaceutical product, KALBITOR© (ecallantide) approved by the FDA (USA), has been released for sale in the year 2009. Jetrea© that is being produced with *P. pastoris* has also been approved by FDA and EMA (EU); and studies to develop new production methods of biopharmaceuticals and their approval applications are being continued.

Promoter genes have been identified by determining the functions of gene sequences in the genome of yeast *P. pastoris* and the wild-type or modified promoter gene sequences have been patented due their industrial potentials.

In the patent numbered U.S. Pat. No. 6,730,499 B1 of the prior art, the *P. pastoris* formaldehyde dehydrogenase (FLD1) promoter that is induced with methanol and/or methylamine has been disclosed. In said patent it is suggested that as the FLD1 promoter can perform production at a comparable level with the $P_{AOX1}$, it can be an alternative to $P_{AOX1}$. *P. pastoris* translation elongation factor (TEF) promoter gene and the recombinant protein production method with this constitutive promoter has protected with the patent numbered U.S. Pat. No. 7,816,509B2.

*P. pastoris* wild-type ADH1 gene and the recombinant protein production processes with this gene has been patented with the patent numbered U.S. Pat. No. 8,222,386B2. The ADH1 promoter subject to the patent is a regulated promoter and it is induced with ethanol and glycerol. The ADH1 gene mentioned in this patent is the same gene with *P. pastoris* wild-type ADH2 gene; however, ADH2 gene is annotated differently in the literature. *P. pastoris* genome annotation is mainly carried out according to functional similarities to the genes in *S. cerevisiae* which is a model organism in yeast research. The gene subject to the present patent, displays functional and structural similarities with *S. cerevisiae* ADH2 gene, thus it's called as ADH2 gene in this application.

Regulated GUT1 (glycerol kinase) promoter gene of the yeast *P. pastoris* has been patented with the patent numbered U.S. Pat. No. 8,785,613B2.

*P. pastoris* DAS promoter variants have been patented with the patent numbered US20110129874A1. These variants have been obtained by the deletion of some promoter gene regions or the insertion of some upstream activating sequence (UAS) gene elements located inside the promoter.

In the patent application numbered WO 2017/021541 A1 of the prior art, *P. pastoris* high-affinity glucose transporter (GTH1) gene promoter (pG1) variants (pG1-x) that are formed by the deletion, insertion or substitution mutations are described.

Mutant AOX1 promoters have been patented with the patent numbered U.S. Pat. No. 9,279,129B2. In this study, the transcription factor binding sites of Hap1, Hsf, Hap234, abaA, Stre, Rapt, Adr1, Mat1 MC, Gcr1 and QA-1F located on promoter gene have been identified and these sequences have been deleted or duplicated to create AOX1 mutants that display activity at a rate of 6% to 160% of the wild-type AOX1 promoter (Hartner et al. 2008).

SUMMARY

The present invention is related to enhanced alcohol dehydrogenase 2 (ADH2) gene promoter-variants by promoter engineering design. *P. pastoris* ADH2 enzyme catalyzes the first step of intracellular ethanol utilization that is oxidation of ethanol to acetaldehyde. Two aspects that are required for the invention are:
  c) design of a sequence, and
  d) selection of the target location in *P. pastoris* genome for integration of the designed module.

Cat8 is an important transcription factor in the activation of genes responsible for ethanol utilization in *Saccharomyces cerevisiae* which is an important ethanol (ethyl alcohol) producing yeast in traditional biotechnology. The present invention is related to the design and construction of $P_{ADH2\text{-}Cat1}$ ($P_{ADH2\text{-}Cat8\text{-}L1}$) and $P_{ADH2\text{-}Cat2}$ ($P_{ADH2\text{-}Cat8\text{-}L2}$) variants by integration of Cat8 transcription-factor-binding-site (TFBS)—"TTCCGTTCGTCCGA" sequence (SEQ ID NO: 3) (Roth et al. 2004)—that is not naturally occurring on the *P. pastoris* wild-type ADH2 promoter, to the targeted positions of *P. pastoris* genome determined by function analysis, and design and construction of the third ADH2 promoter variant ($P_{ADH2\text{-}NucOpt}$) by nucleosome optimization of the wild-type *P. pastoris* ADH2 promoter and recombinant protein production methods thereof.

BRIEF DESCRIPTION OF THE DRAWINGS

FIG. 4 shows the nucleic acid sequence of $PP_{ADH2-wt}$ (SEQ ID NO: 1).

FIG. 5 shows the nucleic acid sequence of $P_{ADH2-NucOpt}$ (SEQ ID NO: 2) with identification of the modified positions.

DETAILED DESCRIPTION OF THE EMBODIMENTS

Figure 1:
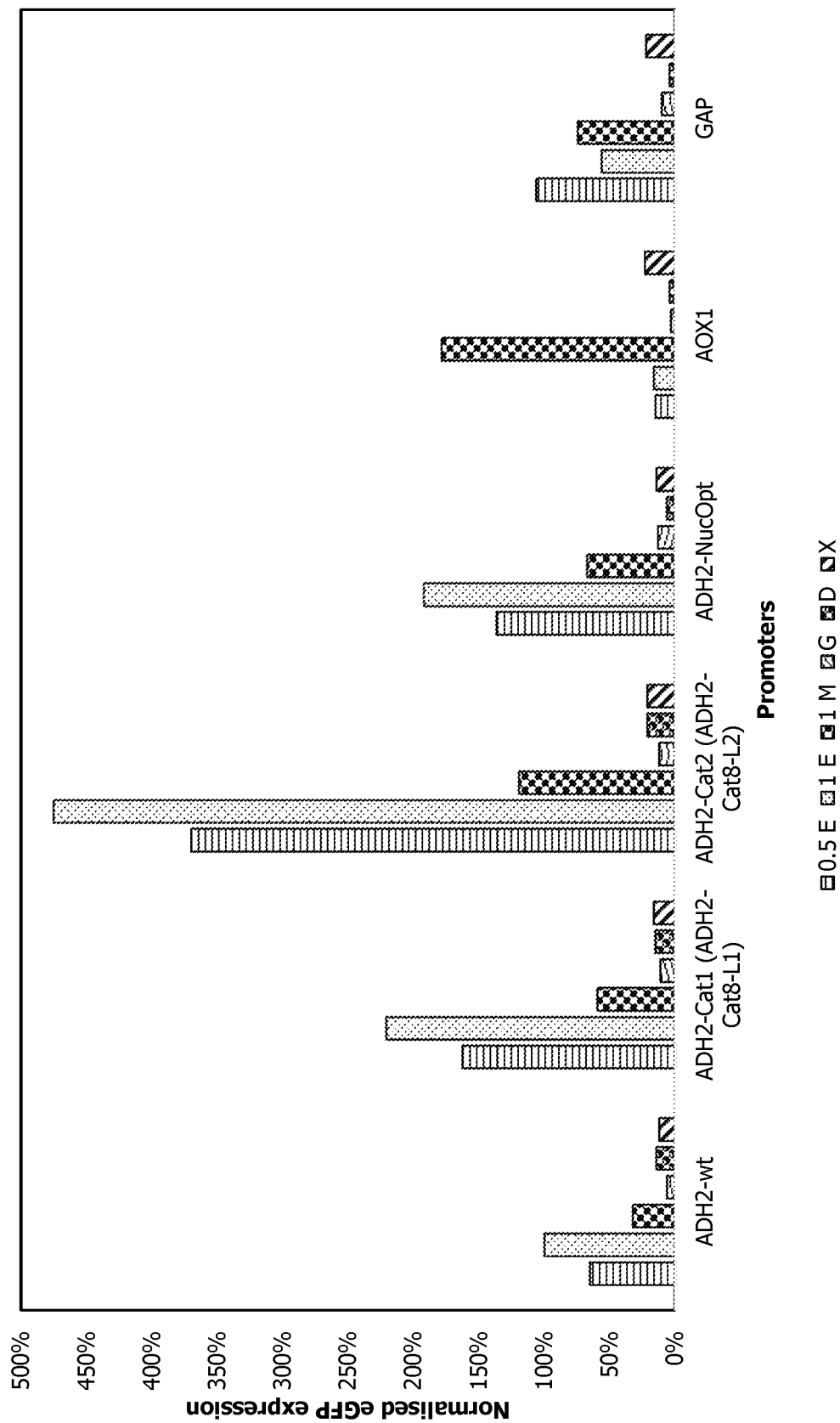
FIG. 1 shows normalized eGFP expressions of *P. pastoris* strains—with respect to eGFP expression in the cells constructed with $P_{ADH2-wt}$ $(0)_{E1}$, constructed with the ADH2 promoter variants, in different carbon sources.
Figure 2:
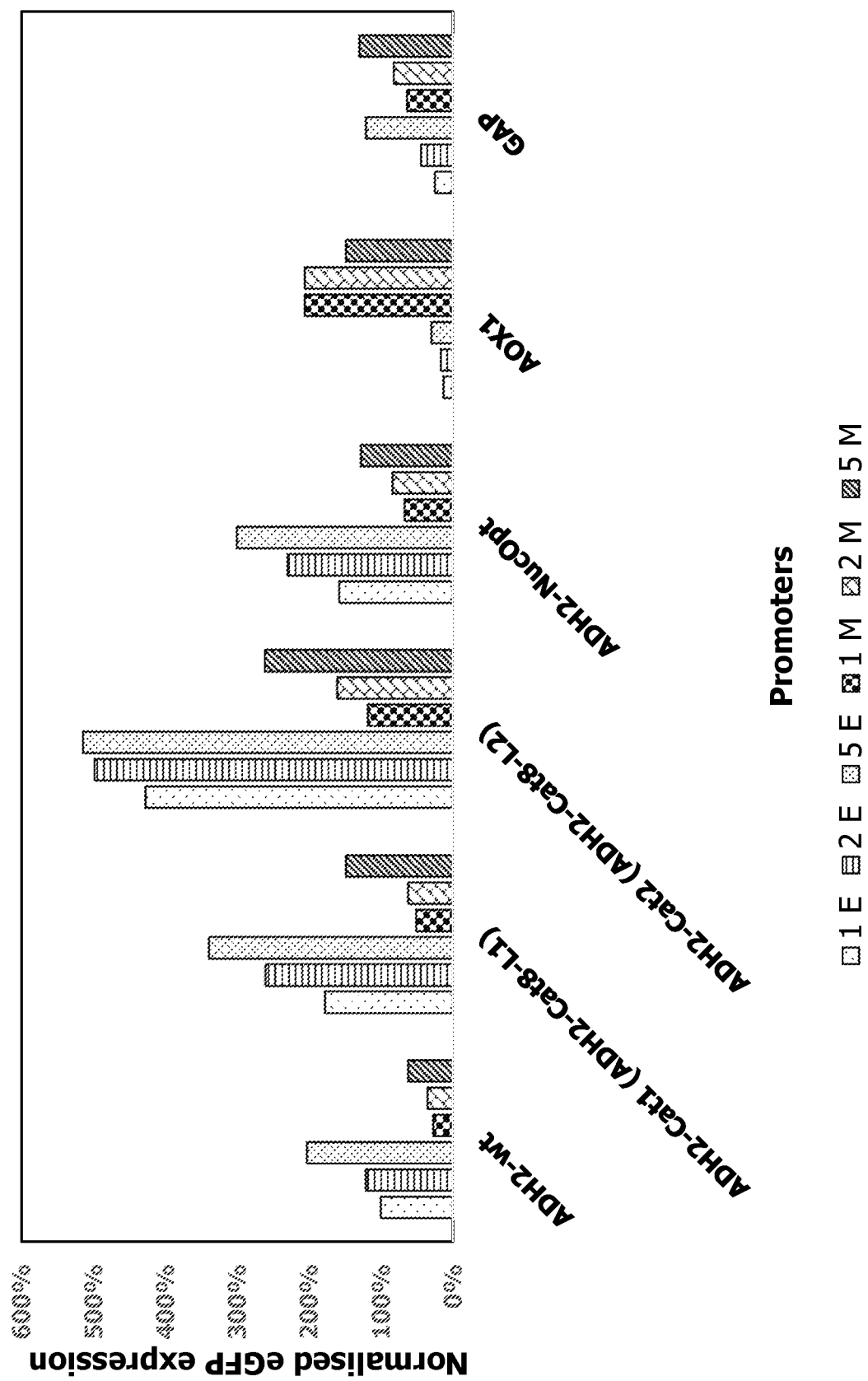
FIG. 2 shows normalized eGFP expressions of *P. pastoris* strains—with respect to eGFP expression in the cells constructed with $P_{ADH2-wt}$ $(0)_{E1}$, constructed with the ADH2 promoter variants, with different ethanol and methanol concentrations.
Figure 3:
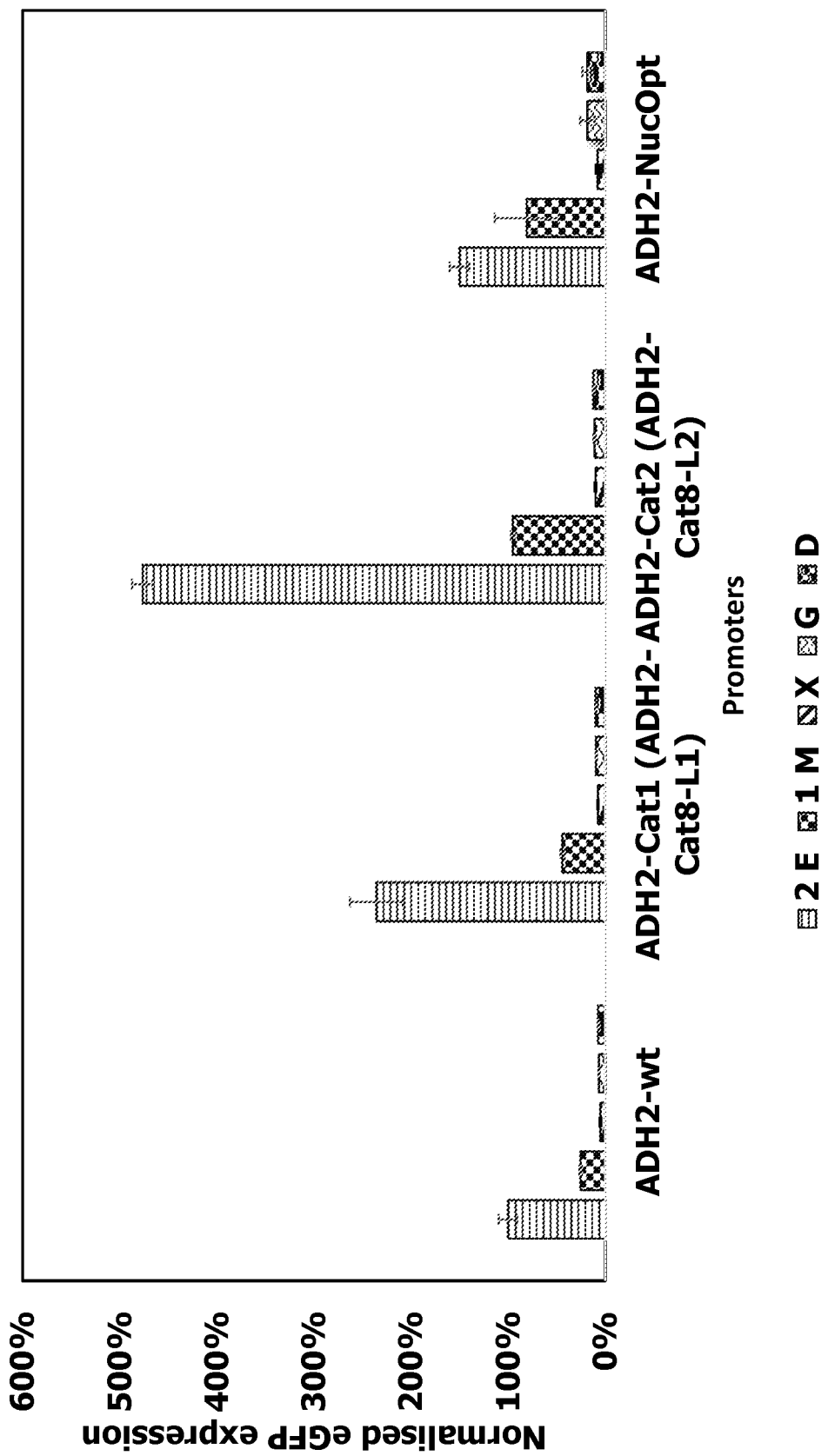
FIG. 3 shows normalized eGFP expressions of *P. pastoris* strains—with respect to eGFP expression in the cells constructed with $P_{ADH2-wt}$ $(0)_{E2}$, constructed with the ADH2 promoter variants, with different ethanol and methanol concentrations.

The productivity of a production process is an important criteria in industrial biotechnology applications. The capacity of the host microorganism to be able to produce the desired recombinant protein is dependent on the promoter architecture. The ideal recombinant protein production system is a system that carries out high yield production in a controlled manner under a strong and regulated promoter gene. The regulated promoters enable the cell growth phase and the recombinant protein production phases to be separated from each other, thereby enhancing the control potential of the process. Moreover the negative effects of the accumulation of recombinant protein in the bioreactor on the growth of cells and their viability is also prevented by separating the two phases.

In *P. pastoris*, the AOX1 promoter, $P_{AOX1}$, system is commonly used. When $P_{AOX1}$ is used, the need to feed toxic alcohol methanol into the bioreactor creates risks. The possibility that there may remain methanol residue in recombinant proteins that have been produced for the food and pharmaceutical industry limits the usage of this method. The prevalent usage of crude enzymes that have not high purity levels in the food industry limits the usage of methanol due to the increasing purification costs in recombinant protein products that are to be used in the food industry. Ethanol is one of the first traditional biotechnological products that have been produced in history of humanity. While the threshold limit value (TLV) permitted for methanol in the working environment of the National Institute for Occupational Safety and Health (NIOSH), USA is 200 ppm, this value for ethanol is 1000 ppm. Moreover while the lethal dose of methanol is 0.3-1 g/kg, the lethal dose of ethanol is 7.060 g/kg. Ethanol is one of the first traditional biotechnological products produced in the history of humanity; and it is known to be safe as it has been used for many years in the chemical, pharmaceutical and food industries and it does not necessitate special precautions in terms of safe process applications.

As the inducing agent of the ADH2 promoter variants subject to the present invention is ethanol, this increases the industrial significance of the variants subject to the present invention as ethanol is both cheap and has a nontoxic and non-hazardous nature. By using the induction and repression properties of the promoter, bioreactor feeding strategies which can be regulated under the ADH2 promoter variants can be developed. In the first phase of the bioreactor operation, by feeding glucose or glycerol that repress the promoter, thereby stopping the recombinant protein production results in high cell density cultures; in the second phase feeding ethanol in increasing concentrations can provide significant promoter induction and effective process control for high cell density recombinant protein production process. Providing an effective process control mechanism and separating the production phase from the cell growth phase have significant advantages in specific cases depending on the features of the heterologous protein to be produced. These advantages are obtaining high protein yield at the end of the process, enhanced product stability, and recombinant protein production in cases where the protein to be expressed is toxic.

The novel and important features of the promoter variants subject to the present invention is that they are stronger than *P. pastoris* wild-type ADH2 promoter ($P_{ADH2-wt}$) and commonly used methanol inducible AOX1 promoter, thus they can produce recombinant proteins in higher amounts compared to commonly used promoter systems. The main aim in recombinant protein production is to develop a high yield production process, and a strong promoter is the most important genetic tool to achieve this aim.

The present invention is related to *Pichia pastoris* alcohol dehydrogenase 2 (ADH2) promoter variants including at least one mutation within nucleotides 1 to 948 (−1047 to −100) of the wild-type *P. pastoris* ADH2 promoter (SEQ ID NO: 1), under ethanol and methanol induction conditions that have stronger expression capacity than wild-type ADH2 promoter.

The present invention includes designed *P. pastoris* ADH2 promoter variants gene sequences comprising *S. cerevisiae* Cat8 TFBS integrated to the specific locations by nucleotide substitutions mentioned below, and the gene sequence of the nucleosome optimized ADH2 promoter variant designed by modifying 100 nucleotides on the wild-type ADH2 promoter. The present invention allows to design original-novel-strategic bioreactor operation conditions for recombinant protein production processes. High cell density recombinant protein production processes by *P. pastoris* can be developed with the promoter variants subject to the present invention: using glucose and glycerol provides high cell concentration and then protein production can be performed with induction under increased ethanol concentrations.

The method of designing promoter variant's *pastoris* ADH2 promoter includes a mutation consisting of integration of a Cat8 transcription factor binding site (TFBS), particularly integration of the "TTCCGTTCGTCCGA" gene sequence (SEQ ID NO: 3) or other gene sequences that show at least 80% similarity with this sequence, at any positions within nucleotides 647 to 660 (−401 to −388); 739 to 752 (−309 to −296); 100 to 1000 (−948 to −48); and mutations specified with SEQ ID NO: 2 within nucleotides 15 to 848 (−1033 to −200) and combinations thereof.

Promoter variant construction is performed by nucleotide mutations which are deletion, substitution, insertion and or inversion.

In the design of ADH2 promoter variants subject to the present invention, the gene sequences that are not naturally occurring on *P. pastoris* wild-type ADH2 promoter have been integrated by substitution to the functionally determined regions of ADH2 promoter. In this study, for the design of promoter variants, Cat8 TFBS, which is optimized for *S. cerevisiae* (Roth et al. 2004), was used for the promoter engineering study of P. *Pastoris* which is a different host. In the design of promoter variant $P_{ADH2-NucOpt}$, a *P. pastoris* promoter has been modified for the first time by nucleosome optimization strategy.

The fundamental advantage of the designed promoter variants is that they are strong and regulated systems; and that they can be induced with nonhazardous ethanol for the food and pharmaceutical industries. Ethanol provides important advantages for the food and pharmaceutical industries as it is a cheap carbon source and it does not create toxicity risks against those working in production processes. Providing efficient process control by means of regulating active (on) and inactive (off) states of promoters with different carbon sources, enables to provide process requirements such as high product yield, product stability and production of toxic proteins to the cell. Production applications that can be conducted with efficient process control provide higher yield and have the potential to provide advantages both in terms of cost and time. The promoter variants subject to the present invention can provide significantly higher recombinant protein production in comparison to the *P. pastoris* wild-type ADH2 promoter gene under ethanol induction condition. Among ADH2 promoter variants, $P_{ADH2-Cat2}$ ($P_{ADH2-Cat8-L2}$) can perform higher production capacities in comparison to the commonly used however toxic-alcohol methanol induced *P. pastoris* alcohol oxidase 1 (AOX1) promoter.

The promoter variants subject to the present invention consist of 1047 nucleotide sequence. When the positions of nucleotides are counted from the first nucleotide at the 5' end, the position of a nucleotide is expressed with a positive number value. However, nucleotides on the promoter can also be determined based on the start of a coding sequence which locates at the end of the promoter, in such a case the first nucleotide (in our case nucleotide A) at the 3' end of the promoter is positioned at "−1", and the nucleotide positions continue to decrease towards the 5' end of the promoter gene, and the first nucleotide (in our case nucleotide T) at the 5' end of the gene is located at −1047 base pair (bp) position.

The nucleotide sequences of the ADH2 promoter variants subject to the present invention have been provided below.
Promoter Variant-1: $P_{ADH2-Cat1}$ ($P_{ADH2-Cat8-L1}$) (SEQ ID NO: 4)

TCCTTTTTACCACCCAAGTGCGAGTGAAACACCCCATGGCTGCTCTCCGA

TTGCCCCTCTACAGGCATAAGGGTGTGACTTTGTGGGCTTGAATTTTACA

CCCCCTCCAACTTTTCTCGCATCAATTGATCCTGTTACCAATATTGCATG

CCCGGAGGAGACTTGCCCCCTAATTTCGCGGCGTCGTCCCGGATCGCAGG

GTGAGACTGTAGAGACCCCACATAGTGACAATGATTATGTAAGAAGAGGG

GGGTGATTCGGCCGGCTATCGAACTCTAACAACTAGGGGGGTGAACAATG

CCCAGCAGTCCTCCCCACTCTTTGACAAATCAGTATCACCGATTAACACC

CCAAATCTTATTCTCAACGGTCCCTCATCCTTGCACCCCTCTTTGGACAA

ATGGCAGTTAGCATTGGTGCACTGACTGACTGCCCAACCTTAAACCCAAA

TTTCTTAGAAGGGGCCCATCTAGTTAGCGAGGGGTGAAAAATTCCTCCAT

CGGAGATGTATTGACCGTAAGTTGCTGCTTAAAAAAAATCAGTTCAGATA

GCGAGACTTTTTTGATTTCGCAACGGGAGTGCCTGTTCCATTCGATTGCA

ATTCTCACCCCTTCTGCCCAGTCCTGCCAATTGCCCATGAATCTGCT<u>TCC</u>

<u>GTTCGTCCGA</u>CCCACCCCCCTTTCCAACTCCACAAATTGTCCAATCTCGT

TTTCCATTTGGGAGAATCTGCATGTCGACTACATAAAGCGACCGGTGTCC

GAAAAGATCTGTGTAGTTTTCAACATTTTGTGCTCCCCCCGCTGTTTGAA

AACGGGGGTGAGCGCTCTCCGGGGTGCGAATTCGTGCCCAATTCCTTTCA

CCCTGCCTATTGTAGACGTCAACCCGCATCTGGTGCGAATATAGCGCACC

CCCAATGATCACACCAACAATTGGTCCACCCCTCCCCAATCTCTAATATT

CACAATTCACCTCACTATAAATACCCCTGTCCTGCTCCCAAATTCTTTTT

TCCTTCTTCCATCAGCTACTAGCTTTTATCTTATTTACTTTACGAAA

The 13 nucleotides marked in the $P_{ADH2-Cat1}$ ($P_{ADH2-Cat8-L1}$) sequence, are not naturally occurring on *P. pastoris* wild-type ADH2 promoter. By means of the 13 nucleotide substitutions, the promoter variant $P_{ADH2-Cat1}$ ($P_{ADH2-Cat8-L1}$) has reached a significantly higher recombinant protein production capacity in comparison to the wild-type *P. pastoris* $P_{ADH2}$ promoter.

Promoter Variant-2: $P_{ADH2-Cat2}$ ($P_{ADH2-Cat8-L2}$) (SEQ ID NO: 5)

TCCTTTTTACCACCCAAGTGCGAGTGAAACACCCCATGGCTGCTCTCCGA

TTGCCCCTCTACAGGCATAAGGGTGTGACTTTGTGGGCTTGAATTTTACA

CCCCCTCCAACTTTTCTCGCATCAATTGATCCTGTTACCAATATTGCATG

CCCGGAGGAGACTTGCCCCCTAATTTCGCGGCGTCGTCCCGGATCGCAGG

GTGAGACTGTAGAGACCCCACATAGTGACAATGATTATGTAAGAAGAGGG

GGGTGATTCGGCCGGCTATCGAACTCTAACAACTAGGGGGGTGAACAATG

CCCAGCAGTCCTCCCCACTCTTTGACAAATCAGTATCACCGATTAACACC

CCAAATCTTATTCTCAACGGTCCCTCATCCTTGCACCCCTCTTTGGACAA

ATGGCAGTTAGCATTGGTGCACTGACTGACTGCCCAACCTTAAACCCAAA

TTTCTTAGAAGGGGCCCATCTAGTTAGCGAGGGGTGAAAAATTCCTCCAT

CGGAGATGTATTGACCGTAAGTTGCTGCTTAAAAAAAATCAGTTCAGATA

GCGAGACTTTTTTGATTTCGCAACGGGAGTGCCTGTTCCATTCGATTGCA

ATTCTCACCCCTTCTGCCCAGTCCTGCCAATTGCCCATGAATCTGCTAAT

TTCGTTGATTCCCACCCCCTTTCCAACTCCACAAATTGTCCAATCTCGT

TTTCCATTTGGGAGAATCTGCATGTCGACTACATAAAG<u>TTC</u>C<u>GTTC</u>GTCC

GAAAAGATCTGTGTAGTTTTCAACATTTTGTGCTCCCCCCGCTGTTTGAA

AACGGGGGTGAGCGCTCTCCGGGGTGCGAATTCGTGCCCAATTCCTTTCA

CCCTGCCTATTGTAGACGTCAACCCGCATCTGGTGCGAATATAGCGCACC

CCCAATGATCACACCAACAATTGGTCCACCCCTCCCCAATCTCTAATATT

CACAATTCACCTCACTATAAATACCCCTGTCCTGCTCCCAAATTCTTTTT

TCCTTCTTCCATCAGCTACTAGCTTTTATCTTATTTACTTTACGAAA

The 7 nucleotides marked in the $P_{ADH2-Cat2}$ ($P_{ADH2-Cat8-L2}$) variant, are not naturally occurring on the wild-type *P. pastoris* ADH2 promoter. The ADH2 promoter variant $P_{ADH2-Cat2}$ ($P_{ADH2-Cat8-L2}$) has reached a significantly higher recombinant protein production capacity in comparison to the wild-type P. pastoris promoter by means of the specified seven nucleotide substitutions in the sequence.

Promoter Variant-3: $P_{ADH2-NucOpt}$ (SEQ ID NO: 2)

The third ADH2 promoter variant subject to the present invention is the nucleosome optimized $P_{ADH2-NucOpt}$ gene. The nucleotides marked in the $P_{ADH2-NucOpt}$ variant sequence are not naturally occurring on the P. pastoris wild-type ADH2 promoter.

TCCTTTTTACCACCTAAGTGCGAGTGAAACACCCTATGGCTGCTCTCCGA

TTGCCCCTCTACAGGCATAAGGGTGTGATTTTTTTTTTTTAATTTTACA

CCCCCTCCAACTTTTTTCGCGTAAATTGATCCTGTTACCAATATTGCATG

CCCGGAGGAGACTTGCCCCCTAATTTCGCGGCGTCGTCCCGGATCGCAGG

GTAAAATATATAGACCCCACAAAAAAAAATGATTATGTAAGAAGAGGG

GGGTGATTCGGCCGGCTATCGAACTCTAACAACTAGGGGGGTGAAAAATG

CCCAGCTTTTTTCCCTATTCTTTGACAAATCAGTATCACTTATTAACACC

CCAAATTTTTTTCTCAACGGTCCCTCATCCTTGCACCCCTCTTTGGACAA

ATGGCAGTTAGTATTAGTGCACTGACTGACTGCCTAACCTTAAACCCTAA

TTTCTTAGAAGGGGCCCATATAGTTAGCGAGGGGTGAAAAATTCCTCCAT

CGGAGATGTATTAACCGTAATTTTTTTTTAAAAAAAAAAAATTCAGATA

GCGAAATTTTTTGATTTCGCGACGCGCGTTTTTTTTTTTTTTTTTTTT

TTTCTCACCCCTTCTGCCCAGTTCTGCCAATTGCCCATGAATCTACTAAT

TTCGTTGATTCCCACCCCCCTTTCCAACTCCAAAAATTTTTTAATTTTTT

TTTTTTTTTGGGAGAATCTGAATGTATATTACATAAAGCGACCGGTGTCC

GAAAAAATTTTTTTTTTTTTAATTTTTTTTTTTCCCCCGCTTTTAAA

AACGGGGGTAAGCGCTCTCCGGGGTGCGAATTCGCGCCCTATTCCTTTCA

CCCTGCCTATTGTAGACGTCAACCCGCATCTGGTGCGAATATAGCGCACC

CCCAATGATCACACCAACAATTGGTCCACCCCTCCCCAATCTCTAATATT

CACAATTCACCTCACTATAAATACCCCTGTCCTGCTCCCAAATTCTTTTT

TCCTTCTTCCATCAGCTACTAGCTTTTATCTTATTTACTTTACGAAA

The technique presented within the scope of the patent numbered U.S. Pat. No. 8,222,386B2 discloses the induction of ADH2 wild-type promoter ($P_{ADH2-wt}$) by glycerol, ethanol or the mixture of these two carbon sources and said that the promoter gene is repressed with glucose and methanol. However, the ADH2 promoter variants subject to the present invention are induced with ethanol and are repressed with glycerol. The regulation of the developed ADH2 promoter variants are differentiated with the below mentioned characteristics according to the prior art:

All designed and constructed ADH2 promoter variants are repressed with glycerol.

The developed ADH2 promoter variants can carry out significantly higher production yield under ethanol induction in comparison to the wild-type ADH2 promoter.

The developed ADH2 promoter variants can be induced with methanol at a medium strength.

The designed ADH2 promoter variants can be induced strongly in the presence of ethanol. Also the developed ADH2 promoter variants are induced in the presence of methanol at medium strength. In production medium where limited glucose, excess glucose, and excess glycerol carbon sources are used, recombinant protein production is repressed. As the designed promoter variants are regulated that can be both induced and repressed, this feature is especially important for the production of toxic proteins to the host cell. Moreover, as it can be induced with non-toxic ethanol, it provides safe-clean-green recombinant protein production conditions.

The ADH2-Cat2 promoter variant is significantly important as it is remarkably strong and it can be strictly regulated with carbon sources. It can even perform more protein production than the most commonly used strong and tightly regulated P. pastoris AOX1 promoter. This situation shows that production yield can be directly increased if potential recombinant protein production (for example production of human growth hormone, serum albumin, insulin and food industry enzymes) is carried out with ADH2-Cat2 (ADH2-Cat8-L2) promoter variant instead of AOX1 promoter. Besides this, significant advantage is provided as the mentioned high efficiency production levels can be achieved with ethanol instead of using toxic methanol for induction of AOX1.

It has been proved by the variants subject to the present invention that S. cerevisiae Cat8 binding site which is not naturally occurring on the wild-type ADH2 promoter gene has an important effect in increasing the expression strength of ADH2 promoter variants. The activating gene modules in yeast promoters are located in the upstream activating sequence site of the promoter. Considering our findings and the yeast promoter architecture, S. cerevisiae Cat8 binding site can be integrated into any position between the 1 to 948 nucleotides of the promoter gene to increase the strength.

The structure of chromatin is one of the most important parameters that regulate gene expression by determining the binding of transcription factors and initiation and elongation of transcription (Li et al. 2007). Nucleosome positioning determines the location and position of nucleosome structures in the genomic DNA sequence (Struhl and Segal, 2013). Nucleosome positioning at genome level, are determined by ATP-dependent nucleosome remodeling enzymes and transcription factors. The nucleosome optimization of P. pastoris wild-type $P_{ADH2}$ gene has been conducted with NuPop and MATLAB software (Xi et al. 2010; Curran et al. 2014). For reliable nucleosome affinity prediction, upstream and downstream gene sequences of $P_{ADH2}$ in the P. pastoris genome has been obtained from the P. pastoris genome database (online access: http://pichiagenome-ext.boku.ac.at:8080/apex/f?p=100:1). Input data for $P_{ADH2}$ was designed starting from 200 bp upstream of the promoter until 100 bp downstream (enhanced green fluorescent protein (eGFP) gene's first 100 nucleotides, since it was used as a reporter protein) of the sequence for more reliable prediction of nucleosome affinity using NuPop. Throughout optimization process, yeast stress responsive elements, carbon source responsive elements, TFBSs related with non-optimal carbon source utilization, core promoter region and originally nucleosome depleted regions were protected from any mutation by defining them as forbidden sites to the optimization algorithm. Also creation or destruction of any known TFBSs were provided throughout optimization process.

EXAMPLES

Example 1

Material and Method

Example 1.1

Designing $P_{ADH2-Cat1}$ ($P_{ADH2-Cat8-L1}$) and $P_{ADH2-Cat2}$ ($P_{ADH2-Cat8-L2}$) Promoter Variants and Cloning with the Reporter Protein Two-step overlap extension polymerase chain reaction (OE-PCR) method was used to integrate Cat8 TFBS to the ADH2 promoter gene and the designed mutagenic primers (Forward_PADH2_Cat1, Reverse PADH2_Cat1, Forward_PADH2_Cat2, Reverse_PADH2_Cat2, Forward_PADH2 and Reverse_PADH2) given below the table have been used to construct $P_{ADH2-Cat1}$ ($P_{ADH2-Cat8-L1}$) and $P_{ADH2-Cat2}$ ($P_{ADH2-Cat8-L2}$) promoter variants.

TABLE 1

Designed primer nucleotide sequences used for the integration of Cat8 TFBS to the designed promoter variants and cloning the promoter variants with eGFP.

| Name of Primer | Primer Nucleotide Sequence | SEQ ID NO: |
|---|---|---|
| Forward_PADH2_Cat1 | CCTGCCAATTGCCCATGAATCTGCTTCCGTTCGTCCGACCC ACCCCCCTTTCCAACTCCACAA | 6 |
| Reverse_PADH2_Cat1 | TTGTGGAGTTGGAAAGGGGGTGGGTCGGACGAACGGAA GCAGATTCATGGGCAATTGGCAGG | 7 |
| Forward PADH2-Cat2 | GTCGACTACATAAAGTTCCGTTCGTCCGAAAAGATCTG | 8 |
| Reverse_PADH2_Cat2 | CAGATCTTTTCGGACGAACGGAACTTTATGTAGTCGAC | 9 |
| Forward_PADH2 | GTCGGATCCCTGCAGTCCTTTTTAC | 10 |
| Reverse_PADH2 | GCCCTTGCTCACCATTTTCGTAAAGTAAATAAGATAAAAGC TAG | 11 |
| Forward_eGFP | CAAAAAACAACTAATTATTCGAAACGAATGGTGAGCAAGG GC | 12 |
| Reverse_eGFP | CGAGGTACCTTACTTGTACAGCTCGTCC | 13 |

The enhanced green fluorescent protein (eGFP) gene has been used as a reporter for determining the gene expression level under the ADH2 promoter variant. The eGFP gene and ADH2 promoter variants gene were amplified by OE-PCR method using the primers (Forward_PADH2, Reverse_PADH2, Forward_eGFP and Reverse_eGFP) given in the table above. Any nucleotide addition between promoter and eGFP gene sequences were prevented. Amplified promoter variant and eGFP gene fragments were digested by using suitable restriction enzymes and were cloned with ligation reaction to the vector which carries a Zeocin™ resistance gene and an AOX1 transcription terminator module. Constructed plasmids were transformed to the chemically competent *Escherichia coli* DH5α cells that have been prepared with the calcium chloride method (Sambrook and Russell, 2001). Putative positive clones were selected using Zeocin™ containing selective LB agar media and following plasmid isolation, constructed recombinant vectors were verified by gene sequencing analysis.

Example 1.2

Transformation of the Yeast *Pichia pastoris* with Recombinant Vectors Carrying Promoter Variants and the Evaluation of the Expression Capacities of Promoter Variants The recombinant vectors containing the ADH2 promoter variant and the eGFP reporter genes were linearized with the Bg/II restriction enzyme according to the suggestions of the manufacturer and the competent *P. pastoris* X33 cells prepared with the lithium chloride method were transfected with linearized gene fragments (Invitrogen, 2000). After regeneration, the transformants were inoculated into selective Zeocin™ containing YPD Agar medium. Following transformation, putative clones carrying the expression cassette comprising the promoter variant gene and the eGFP reporter gene was verified with colony PCR and at least 10 individuals were selected from each strain and used to evaluate the production capacities of promoter variants.

The expression cassette comprises at least one ADH2 promoter variant and at least a nucleic acid molecule encoding a protein (peptide) or functional nucleotide, said promoter variant and nucleic acid molecule form single- or multi-copy expression cassette. These Nucleic acid molecule and promoter are operably linked together.

The vector carrying the Zeocin™ resistance gene and an AOX1 transcription terminator module, comprises *Pichia pastoris* alcohol dehydrogenase 2 (ADH2) promoter variant and at least a nucleic acid molecule in the expression cassette.

*Pichia pastoris* cells were precultivated in YP medium (10 g/L yeast extract, 20 g/L peptone) for 20 hours at 25° C. at 280 rpm before being transferred to the production medium. At the end of the precultivation, cells were harvested by centrifugation and transferred to the production medium. In order to evaluate the expression capacities of the promoter variants a minimal medium (6.3 g/L $(NH_4)_2HPO_4$; 0.8 g/L $(NH_4)_2SO_4$; 0.49 g/L $MgSO_4*7H_2O$; 2.64 g/L KCl; 0.0535 g/L $CaCl_2*2H_2O$; 22 g/L citric acid monohydrate; 1.47 ml/L PTM1; 2 ml/L biotin (0.2 g/L); 20 ml $NH_4OH$ (25%)) including 5 different carbon sources separately was used. Different substrates used and the production parameters applied in the production trial were given in the table below. A production medium including m2p kit polysaccharide 25% (v/v) and 0.7% (v/v) enzyme (m2p-labs GmbH, Germany) mixture was used for limited glucose condition.

TABLE 2

Production test parameters applied in order to compare the eGFP production capacities of promoter variants with Pichia pastoris.

| Condition | ID | Initial $OD_{600}$ Value | Production Substrate | Production Time |
|---|---|---|---|---|
| Excess glycerol | G | 0.1 | 2 g/L glycerol | 20 hours |
| Excess glucose | D | 0.1 | 2 g/L glycerol | 20 hours |
| Limited glucose | X | 1 | Limited glucose concentration | 20 hours |
| Methanol | 1M | 1 | 1% (v/v) methanol | 20 hours |
| Ethanol | 0.5E | 1 | 0.5% (v/v) ethanol | 20 hours |
| Ethanol | 1E | 1 | 1% (v/v) ethanol | 20 hours |
| Ethanol | 2E | 1 | 2% (v/v) ethanol | 20 hours |

Production tests having different ethanol and methanol concentrations mentioned below, have been carried out in order to compare the production potentials of promoter variants to commonly used promoters with increasing alcohol concentrations. The substrate that was used in production media was supplied at t=0 hour which is the initiation of the production and at the end of the 20th hour eGFP production amounts of the cells were analyzed.

TABLE 3

Production test parameters applied in order to compare the eGFP production capacity of promoter variants with different ethanol and methanol concentrations with Pichia pastoris.

| Condition | ID | Initial $OD_{600}$ Value | Production Substrate | Production Time |
|---|---|---|---|---|
| Ethanol 0.5 | 0.5 E | 1 | 0.5% (v/v) ethanol | 20 hours |
| Ethanol 1 | 1 E | 1 | 1% v/v ethanol | 20 hours |
| Ethanol 2 | 2 E | 1 | 2% v/v ethanol | 20 hours |
| Ethanol 5 | 5 E | 1 | 5% (v/v) ethanol | 20 hours |
| Methanol 1 | 1 M | 1 | 1% v/v methanol | 20 hours |
| Methanol 2 | 2 M | 1 | 2% v/v methanol | 20 hours |
| Methanol 5 | 5 M | 1 | 5% (v/v) methanol | 20 hours |

The cells were cultured in 2 ml production media including different carbon source in 24 deep-well-plates (24 deep-well-plate, Whatman, UK) for 20 hours at a mixing speed of 280 rpm and at a temperature of 25° C. At the end of the 20th hour, Pichia pastoris cells were diluted in a phosphate-buffered saline solution to the $OD_{600}$ value of 0.4.

Intracellular eGFP production values were determined by measuring average eGFP fluorescence per unit cell using Guava easyCyte™ (MilliPore) flow cytometry. In flow cytometry eGFP was stimulated at 488 nm and the emission value was collected at 525 nm. Fluorescence signal from 10,000 cells were taken into account in each measurement, using FSC and SSC values, cells which define the yeast cluster in the graphic were selected and the cells that show linear regression in terms of FSC-H and FSC-A values were gated to select singlets. Fluorescence intensity based on the cell volume and geometric mean of the gated population were used in eGFP fluorescence calculations for determination of the specific eGFP synthesis levels of the cells. Relative eGFP expression levels were calculated compared to eGFP expression under wild-type ADH2 promoter.

These cells comprise least one Pichia pastoris alcohol dehydrogenase 2 (ADH2) promoter variant at least an expression cassette and at least a vector. Said cell is a eukaryotic cell, particularly a yeast cell, preferably a methylotrophic yeast cell, preferably a yeast cell selected from the group consisting of Pichia, Candida, Hansenula and Toruplosis, especially a Pichia pastoris cell.

Recombinant proteins, peptide or functional nucleic acid are expressed by the following steps:

Production of ADH2 promoter variants,
Production of expression cassette with the addition of eGFP reporter gene,
Production of recombinant vector promoter variants,
Transformation of eukaryotic cells especially yeast cell, preferably a methylotrophic yeast cell, preferably a yeast cell selected from the group consisting of Pichia, Candida, Hansenula and Toruplosis, especially a Pichia pastoris cell with the recombinant vector and culturing the transformed cells in a suitable medium,
Preferably inducible expression of said protein, peptide or functional nucleic acid molecule,
Isolation of the produced protein, peptide or functional nucleic acid molecule.

Example 2

Results

The recombinant protein (eGFP) production under the promoter variants subject to the present invention were tested with shake flask bioreactor experiments. Production capacities of the designed promoter variants were compared with commonly used P. pastoris inducible AOX1 and constitutive GAP promoters, and the results are given in Table 4. Effect of different carbon sources on the activity of the promoter variants and thus efficiency of recombinant protein production were evaluated. Productivities of promoter variants are given in the Table 4, eGFP production by wt-ADH2 promoter under 1% (v/v) ethanol induction was determined as 100 unit and productivities of variants were related to this value.

TABLE 4 eGFP production capacities of the designed $P_{ADH2}$ variants in yeast P. pastoris with different carbon sources

| Promoter | 0.5 E | 1 E | 1 M | X | G | D |
|---|---|---|---|---|---|---|
| Wt-ADH2 | 65% | 100% | 32% | 12% | 6% | 14% |
| ADH2-Cat1 (ADH2-Cat8-L1) | 162% | 221% | 59% | 16% | 11% | 15% |
| ADH2-Cat2 (ADH2-Cat8-L2) | 370% | 475% | 119% | 21% | 12% | 21% |
| ADH2-NucOpt | 136% | 192% | 67% | 14% | 13% | 6% |
| AOX1 | 15% | 16% | 178% | 23% | 3% | 4% |
| GAP | 106% | 56% | 74% | 22% | 10% | 4% |

According to the results in Table 4, increasing ethanol concentrations from 0.5% to 1% (v/v) has increased the eGFP expression level of $P_{ADH2-wt}$ and promoter variants around 28-53%. When P. pastoris cells are induced with 1% (v/v) ethanol, eGFP production capacity of $P_{ADH2-Cat1}$ ($P_{ADH2-Cat8-L1}$), $P_{ADH2-Cat2}$ ($P_{ADH2-Cat8-L2}$), and $P_{ADH2-NucOpt}$ was respectively, 2.21-, 4.75-, and 1.92-fold higher than that of wt-ADH2 promoter. Even though productivities of ADH2 promoter variants are lower under 1% (v/v) methanol induction in comparison to ethanol induction, they can still perform medium strength productivity. The activities of promoter variants are severely reduced under limited glucose, excess glycerol and excess glucose conditions; in other words, the promoter variants are repressed under such conditions.

The effect of different ethanol and methanol concentrations on recombinant protein production by $P_{ADH2}$ variants were evaluated with shake flask bioreactor experiments and the eGFP production results are presented in Table 5.

TABLE 5 eGFP production capacities of the designed $P_{ADH2}$ variants in yeast *P. pastoris* with different ethanol and methanol concentrations

| Promoter | 1 E | 2 E | 5 E | 1 M | 2 M | 5 M |
|---|---|---|---|---|---|---|
| Wt-ADH2 | 100% | 121% | 203% | 27% | 35% | 62% |
| ADH2-Cat1 (ADH2-Cat8-L1) | 178% | 260% | 339% | 51% | 62% | 149% |
| ADH2-Cat2 (ADH2-Cat8-L2) | 427% | 498% | 514% | 118% | 161% | 261% |
| ADH2-NucOpt | 158% | 230% | 300% | 67% | 84% | 128% |
| AOX1 | 13% | 17% | 30% | 206% | 206% | 149% |
| GAP | 25% | 44% | 121% | 64% | 82% | 130% |

According to the results presented in Table 5, in increasing ethanol concentration up to 5%, the production capacity of $P_{ADH2-wt}$ and promoter variants continues to increase. However, the production capacity of the AOX1 promoter which is the most commonly used *P. pastoris* promoter does not increase with increasing methanol concentrations under the tested conditions, and besides this, the growth of *P. pastoris* cells that have been induced with 5% (v/v) methanol is hampered and the cells start to die. The resistance of *P. pastoris* against high concentrations of ethanol is higher in comparison to methanol. This result shows that the designed promoter variants can be used for high yield recombinant protein production processes in fully controlled bioreactors using high concentrations of ethanol.

Production experiments using different carbon sources were performed with 3 biological replicas of each *P. pastoris* strain comprising each promoter variant and the results are presented in Table 6.

TABLE 6 eGFP production capacities of designed $P_{ADH2}$ variants in *P. pastoris* with different carbon sources

| Promoter | 2 E | 1 M | X | G | D |
|---|---|---|---|---|---|
| wt-ADH2 | 100 ± 10 | 25 ± 1 | 5 ± 1 | 6 ± 1 | 7 ± 0 |
| ADH2-Cat1 | 236 ± 27 | 44 ± 2 | 7 ± 1 | 9 ± 1 | 10 ± 0 |
| ADH2-Cat2 | 476 ± 11 | 95 ± 2 | 10 ± 1 | 11 ± 1 | 12 ± 1 |
| ADH2-NucOpt | 150 ± 10 | 80 ± 33 | 8 ± 2 | 18 ± 7 | 18 ± 5 |

Under 2% (v/v) ethanol induction condition, $P_{ADH2-Cat1}$ ($P_{ADH2-Cat8-L1}$), $P_{ADH2-Cat2}$ ($P_{ADH2-Cat8-L2}$), and $P_{ADH2-NucOpt}$ performed respectively 2.36-, 4.76-, and 1.50-fold higher eGFP production in comparison to that of wt-ADH2 promoter. The designed promoter variants have reached significantly higher production capacities under ethanol and methanol induction condition in comparison to $P_{ADH2-wt}$ while they still maintain their regulated nature by being repressed in the presence of limited glucose, excess glycerol and excess glucose.

REFERENCES

Ahmad, M., Hirz, M., Pichler, H., & Schwab, H. (2014). Protein expression in *Pichia pastoris*: recent achievements and perspectives for heterologous protein production. *Applied microbiology and biotechnology,* 98(12), 5301-5317.

Curran, K. A., Crook, N. C., Karim, A. S., Gupta, A., Wagman, A. M., & Alper, H. S. (2014). Design of synthetic yeast promoters via tuning of nucleosome architecture. Nature communications, 5.

Hartner, F. S., Ruth, C., Langenegger, D., Johnson, S. N., Hyka, P., vd. (2008). Promoter library designed for fine-tuned gene expression in *Pichia pastoris*. *Nucleic acids research,* 36(12), e76-e76.

Invitrogen (2010), EasySelect™ *Pichia* Expression Kit For Expression of Recombinant Proteins Using pPICZ and PPICZα in *Pichia pastoris*

Li, B., Carey, M. and Workman, J. L. (2007). The role of chromatin during transcription. *Cell* 128: 707-719.

Roth, S., Kumme, J., and Schüller, H. J. (2004). Transcriptional activators Cat8 and Sip4 discriminate between sequence variants of the carbon source-responsive promoter element in the yeast *Saccharomyces cerevisiae*. *Current genetics,* 45(3), 121-128.

Sambrook, J., Russell, D. W. (2001) "Molecular cloning: a library manual", $3^{rd}$edn., Cold Spring Harbor Library Press, Cold Spring Harbor, New York Struhl, K., and Segal, E. (2013). Determinants of nucleosome positioning. *Nature structural and molecular biology,* 20(3), 267-273.

Xi, L., Fondufe-Mittendorf, Y, Xia, L., Flatow, J., Widom, J., & Wang, J. P. (2010). Predicting nucleosome positioning using a duration Hidden Markov Model. BMC bioinformatics, 11(1), 1.

What is claimed is:

1. A *Pichia pastoris* alcohol dehydrogenase 2 (ADH2) promoter variant, comprising at least one mutation, wherein the at least one mutation is from integration of a Cat8 transcription factor binding site (TFBS) at any positions within nucleotides 647 to 660; or 739 to 752 of SEQ ID NO: 1, wherein the Cat8 TFBS is set forth by SEQ ID NO: 3.

2. The *Pichia pastoris* ADH2 promoter variant-according to claim 1, wherein in the mutation, nucleotides are mutated by deletion, substitution, insertion and/or inversion.

3. An expression cassette, comprising at least one *Pichia pastoris* ADH2 promoter variant according to claim 1; and at least a nucleic acid molecule encoding a recombinant protein, a peptide or a functional nucleotide, wherein the *Pichia pastoris* ADH2 promoter variant and the nucleic acid molecule form a single- or multi-copy expression cassette.

4. The expression cassette according to claim 3, wherein the *Pichia pastoris* ADH2 promoter variant and the nucleic acid molecule are operably linked together.

5. The expression cassette according to claim 3, wherein in the mutation, nucleotides are mutated by deletion, substitution, insertion and/or inversion.

6. A vector, comprising the *Pichia pastoris* alcohol dehydrogenase 2 (ADH2) promoter variant according to claim 1 and at least a nucleic acid molecule encoding a recombinant protein, a peptide or a functional nucleotide.

7. The vector according to claim 6, wherein in the mutation, nucleotides are mutated by deletion, substitution, insertion and/or inversion.

8. A cell, comprising the *Pichia pastoris* alcohol dehydrogenase 2 (ADH2) promoter variant according to claim 1 and an expression cassette or a vector,
wherein the expression cassette comprises the *Pichia pastoris* ADH2 promoter variant and at least a nucleic acid molecule encoding a recombinant protein, a peptide or a functional nucleotide, and
the vector comprises the *Pichia pastoris* ADH2 promoter variant and at least the nucleic acid molecule encoding the recombinant protein, the peptide or the functional nucleotide.

9. The cell according to claim 8, wherein in the mutation, nucleotides are mutated by deletion, substitution, insertion and/or inversion.

10. The cell according to claim 8, wherein the cell is an eukaryotic cell, wherein the eukaryotic cell is a methylotrophic yeast cell, wherein the methylotrophic yeast cell is selected from the group consisting of *Pichia, Candida, Hansenula* and *Toruplosis*.

11. An expression method of a recombinant protein, a peptide or a functional nucleic acid, comprising the following steps of:

providing an expression cassette or a vector, wherein the expression cassette comprises the *Pichia pastoris* ADH2 promoter variant according to claim 1 and at least a nucleic acid molecule encoding the recombinant protein, the peptide or the functional nucleic acid, wherein the *Pichia pastoris* ADH2 promoter variant and the nucleic acid molecule form a single- or multi-copy expression cassette; the vector comprises the *Pichia pastoris* ADH2 promoter variant and at least the nucleic acid molecule;

transforming a cell with the vector or the expression cassette to obtain a transformed cell, wherein the transformed cell comprises at least one *Pichia pastoris* alcohol dehydrogenase 2 (ADH2) promoter variant and the expression cassette or the vector;

culturing the transformed cell in a suitable medium,
inducing an expression of the recombinant protein, the peptide or the functional nucleic acid,
isolating the recombinant protein, the peptide or the functional nucleic acid.

12. The expression method according to claim 11, wherein the cell is an eukaryotic cell, and the eukaryotic cell is a methylotrophic yeast cell selected from the group consisting of *Pichia, Candida, Hansenula* and *Toruplosis*.

13. The expression method according to claim 11, wherein in the mutation, nucleotides are mutated by deletion, substitution, insertion and/or inversion.

14. The expression method according to claim 11, wherein in the expression cassette, the *Pichia pastoris* ADH2 promoter variant and the nucleic acid molecule are operably linked together.

* * * * *